United States Patent [19]

Nelson

[11] 4,240,282
[45] Dec. 23, 1980

[54] COMBINED LEVEL INDICATOR AND HYDROMETER

[75] Inventor: John F. Nelson, New Lenox, Ill.
[73] Assignee: Illinois Tool Works Inc., Chicago, Ill.
[21] Appl. No.: 79,639
[22] Filed: Sep. 27, 1979
[51] Int. Cl.³ .............................................. G01N 9/12
[52] U.S. Cl. .......................................... 73/447; 73/291
[58] Field of Search ................. 73/447, 293, 451, 291, 73/327, 453

[56] References Cited

U.S. PATENT DOCUMENTS

| 3,597,972 | 8/1971 | Ryder | 73/291 |
| 3,597,973 | 8/1971 | Ryder | 73/291 |
| 3,893,339 | 7/1975 | Melone | 73/327 |
| 3,915,753 | 10/1975 | Melone | 73/327 |
| 3,954,010 | 5/1976 | Hilblom | 73/447 |

*Primary Examiner*—Donald O. Woodiel
*Attorney, Agent, or Firm*—J. R. Halvorsen; T. W. Buckman

[57] ABSTRACT

There is disclosed a new and improved combined liquid level indicator and hydrometer which includes a light transmitting member having an indicating surface and a reflector surface. The reflector surface is adapted to be submerged in liquid for reflecting light to the indicating surface when the liquid is below a predetermined level. The liquid level indicator and hydrometer further includes a chamber aligned with and partially receiving the reflector surface. The chamber confines and positions a float member relative to the reflector surface for being viewed through the indicating surface responsive to the relative specific gravity of the liquid. A connection means carried by the chamber supports the light transmitting member and aligns the reflector surface with respect to the chamber. The chamber is initially formed in an open condition adapted for accepting the float member therein and is lockable thereafter for capturing the float member within the chamber. As a result, the chamber is arranged to receive the float member and confine the float member therein independently of the mounting of the light transmitting member to the chamber.

9 Claims, 6 Drawing Figures

COMBINED LEVEL INDICATOR AND HYDROMETER

BACKGROUND OF THE INVENTION

The present invention relates to an improved combined liquid level indicator for indicating levels of liquids subject to fluctuation and hydrometer means for indicating the specific gravity of the liquid.

It is frequently necessary to check the level of the electrolytic in storage batteries installed in vehicles or the like and the anti-freeze level in cooling systems of vehicles. Likewise it is frequently necessary to check the specific gravity of the electrolyte in storage batteries, preferably, at the same time as the liquid level is determined and similarly, to determine the specific gravity of the liquid in the cooling systems wherein the coolant may be various forms of commercial anti-freezes. As is well known, the usual practice for checking the liquid level or specific gravity in either storage batteries or cooling systems contemplates the removal of the filling caps from the battery or from the radiator so as to permit a look inside. Various devices have heretofore been proposed for aiding the checking of the liquid level in batteries and radiators or the like. Devices have also been suggested for checking the specific gravity of the electrolytic or coolant. Also, U.S. Pat. Nos. 3,597,973 and 3,893,339 which are assigned to the assignee of the present invention fully describe a combined liquid level indicator and hydrometer means for checking both the level and specific gravity of a liquid and cap means for use with sealed batteries.

Devices of the last mentioned variety generally include a light transmissive member having an external indicating surface and a reflecting surface adapted to be submerged into the liquid. When the liquid is below a predetermined level, light is reflected from the reflecting surface to the indicating surface. Devices of the last mentioned variety also include a cage or chamber connected to the light transmissive member which cage or chamber confines a float member. The light transmissive member is aligned with the chamber and the float member is movable relative to the reflecting surface for indicating the relative specific gravity of the liquid. In one position, the float member is viewable through the indicating surface of the light transmissive member for indicating that the specific gravity of the liquid is above a predetermined specific gravity. In a second position, the float member is out of view from the light transmissive member so that it cannot be seen through the indicating surface to indicate that the specific gravity of the liquid is below a predetermined specific gravity.

Devices which provide a combined indication of liquid level and specific gravity have become very popular in use due to the convenience of checking both liquid level and liquid specific gravity simultaneously. However, prior devices of this kind have been inconvenient to assemble because, during assembly, it is necessary to mount the light transmissive member upon the chamber or cage at the same time that the float member is placed into the cage. As a result, the float members which usually comprise a rather small diameter plastic ball may escape from the chamber during assembly. This of course is undesirable inasmuch as such a device without the float ball is incapable of providing an indication of specific gravity.

It is therefore a general object of the present invention to provide an improved combined fluid level indicator and hydrometer.

It is a more specific object of the present invention to provide an improved combined fluid level indicator and hydrometer which may be readily assembled.

The present invention therefore provides a combined liquid level indicator and hydrometer comprising light transmitting means including indicating means and reflector means adapted to be submerged in liquid for reflecting light to the indicating means when the liquid is below a predetermined level, a float member, chamber means aligned with the reflector means and arranged to confine and position the float member relative to the reflector means for being viewed through the indicating means responsive to the relative specific gravity of the liquid, and connection means for supporting the light transmitting means and aligning the reflector means with the chamber means. The chamber means includes a hinged closure means carrying a moveable wall that is operative independently of the connection means and pivotal between an opened position and a closed position to define a wall for confining the float member within the chamber means.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in connection with the accompanying drawings, in the several figures of which like reference numerals identify identical elements, and wherein:

DESCRIPTION OF THE PREFERRED EMBODIMENT

Figure 1:
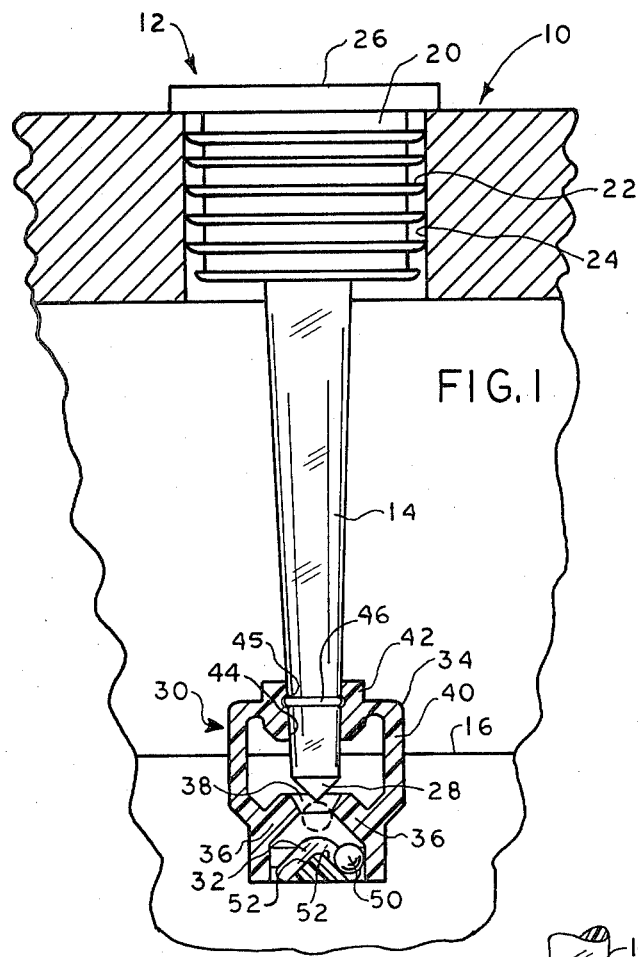
FIG. 1 is a front elevational view, partly in cross-section, of an improved combined liquid level indicator and hydrometer embodying the present invention.
Figure 5:
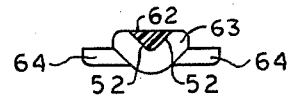
FIG. 5 is a sectional view taken along lines 5—5 of FIG. 3.

Referring now to FIG. 1, a storage battery, automotive radiator or other container 10 is shown utilizing a combined fluid level indicator and hydrometer means 12 embodying the present invention for indicating the level of the liquid subject to fluctuations and also the specific gravity of the liquid. The combined liquid level indicator and hydrometer includes a light transmissive member or rod 14 which is formed from a light transmitting material such as an acrylic, glass, styrene or other clear or partially clear materials. The rod 14 is preferably elongated so that it may be mounted in a wall of the battery or fluid vessel, or in the fluid cap of a battery with an upper end thereof exposed and a lower end thereof projecting downwardly at least to a minimum desired level 16 of liquid 18 within the vessel 10. In this embodiment, the rod 14 is carried by a cylindrically shaped member 20 having an external ribs 22 for being frictionally received in sealing relationship with a corresponding opening 24 of the vessel 10. The rod 14 includes an indicating surface at its upper end 26 which is external to the container 10 and a light reflecting cone-shaped tip surface 28 which is arranged to be submerged within the liquid 18.

The included angle of the conical tip 28 is 90° and therefore, any light rays passing downwardly through the liquid level indicator member 14 may be received by the conical surface and deflected horizontally to the oppositely disposed portion of the conical surface and then reflected upwardly to the top viewing surface or indicating surface 26. This assumes, however, that the portion of the conical surface receiving and reflecting light rays is not immersed within the liquid of the container 10. Any portion of the conical tip section 28 immersed within the body of the liquid of the container will prevent the reflection of light rays as is known in the art. Hence such portion will be indicated by a complementary shaded portion at the indicating surface 26.

Referring now to FIGS. 2-6 in addition to FIG. 1, it will be noted that the combined liquid level indicator and hydrometer further includes a cage or chamber means 30 which is mounted to the end of the light tranmissive member 14. The cage 30 includes a lower chamber 32 and an upper portion 34 integrally formed therewith. Separating the upper portion 34 from the lower chamber 32 is an upper wall 36 which is vertically inclined. Within the upper wall 36 there is provided a tapered aperture 38 which permits access of the conical tip 28 of the light transmissive member 14 to the lower chamber 32.

The light transmissive member 14 is supported and aligned with respect to the aperture 38 by a support or connecting means 40 of the upper portion 34. The support means 40 comprises a pair of upwardly extending side walls which include and secure a collar 42. The collar includes a through bore 44 which is in axial alignment with the aperture 38 and dimensioned for tightly receiving the light transmissive member 14 therein. In the wall of bore 44 there is provided an annular groove 45 adapted to accept a complementary annular rib 46 carried by member 14. This arrangement insures positive assembly of member 14 and cage 30 with tip section 28 properly positioned relative to aperture 38.

As will also be noted in FIG. 1, the lower chamber 32 is arranged to confine a float ball 50 therein. The float ball or member 50 is formed from plastic having a predetermined and known specific gravity and is slightly smaller in diameter than the minimum diameter dimension of the aperture 38. As will be further noted from FIG. 1, the lower chamber 32 also includes a back wall 47 and lower wall portions 52 which are substantially parallel to the upper wall portions 36. As a result, the wall portions 36 and 52 form a pair of spaced vertically inclined wall means which serve to position the float ball 50 as will be described hereinafter in response to the specific gravity of the liquid 18.

In operation, if the specific gravity of the liquid 18 is below a known and predetermined specific gravity, the float ball 50 will assume the position as indicated by the solid lines. In this position, the float ball 50, which may preferably be red, blaze orange, green, or any other desired color to facilitate viewing, will be out of view from the light transmissive member 14. Hence, the float ball 50 will not be viewable through the indicating surface 26.

If the specific gravity of the liquid 18 is above a predetermined and known specific gravity, the float ball 50 will float upwardly and be guided by the vertically inclined walls to its dashed line position. In this position, the float ball 50 is aligned with the aperture 38 and reflecting surface 28 of the light transmissive member 14, the latter blocking aperture 38, and the ball 50 will be viewable through the indicating surface 26. As a result, both the liquid level and the specific gravity of the liquid may be checked simultaneously.

Figure 6:
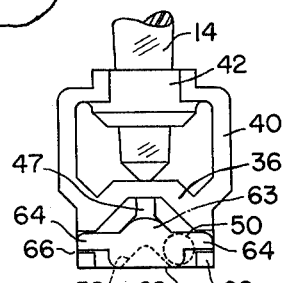
FIG. 6 is a partial front elevational view of the device of FIG. 1 in assembled condition.
Figure 3:
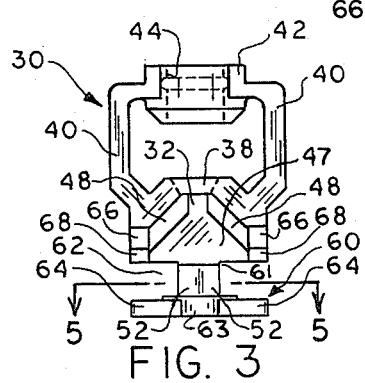
FIG. 3 is a front elevational view of the cage or chamber means of the combined level indicator and hydrometer of FIG. 1 as it is molded.
Figure 4:
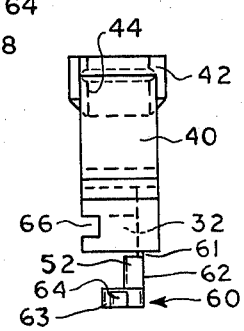
FIG. 4 is a side view of the cage or chamber means of FIG. 3.

In FIG. 3 it can be noted that the cage 30 includes a hinged closure means 60 in the form of a thinned portion 61 hingedly connected to the lower edge of back wall 47 and the wedge shaped bottom wall 62. The bottom wall 62 includes the inclined surfaces 52 and is molded in an initially opened condition as illustrated in FIGS. 3 and 4. The hinged bottom further includes an upstanding triangular shaped flange 63, similar in size and configuration to back wall 47 and adapted to form a front wall spaced from back wall 47. Wall 63 also has extending laterally therefrom a pair of bar-like extensions 64 which are arranged to be latchingly received by a pair of slots 66 formed in the side walls 68 of the lower chamber 32. The lower chamber also includes a plurality of openings 48 in back wall 47, smaller than said predetermined diameter of ball 50, to permit the liquid 18 to enter the lower chamber 32. The upper edges of front wall 63 as viewed in FIG. 6 are similarly spaced from upper wall portions 36 a distance less than said predetermined diameter of ball 50 and also permit access for liquid into said cage chamber 32.

In one method of assembly, before the float ball 50 is administered to the lower chamber, the light transmissive member 14 is inserted into the bore 44 of the collar 42. The light transmissive member 14 is inserted into the bore 44 by a sufficient distance to cause the annular rib 46 to be accepted in the complementary groove 45 whereby the light reflecting tip 28 is aligned with and blocks the aperture 38 as best illustrated in FIG. 1.

Figure 2:
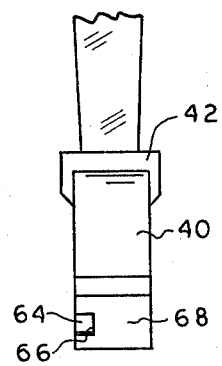
FIG. 2 is a partial side elevational view of the device of FIG. 1.

To complete the assembly of the hydrometer, it must be remembered that the cage 30 is initially molded or formed with the hinged closure means 60 being in an opened condition as illustrated in FIG. 3. The float ball 50 can then be placed into the lower chamber 32 and then the bottom wall 62 pivoted about hinge 61 from its opened position as illustrated in FIGS. 3 and 4 to its closed position as illustrated in FIGS. 2 and 6. When the hinged closure means 60 is in the closed position, the extensions 64 are lockingly received within the recesses 66 of the lower chamber side walls 68. As a result, the float ball 50 is confined within the lower chamber 32 with the hinged closure means 60 being securely locked. Assembly of the hydrometer is now complete.

An alternate method of assembly is to move the hinged closure means to its closed position with the extensions 64 lockingly received within the recesses 66; the float ball 50 being introduced into lower chamber 32 through aperture 38; and the light transmissive member 14 inserted into the bore 44 until the light reflecting tip 28 is aligned with and blocks aperture 38. Assembly of the hydrometer is now complete.

From the foregoing, it can be appreciated that the present invention provides a new and improved liquid level indicator and hydrometer. The combined liquid level indicator and hydrometer of the present invention allows the light transmissive member 14 and the float ball 50 to be rapidly mounted with respect to the cage 30 independently of one another. Positive retention of the ball is readily accomplished and escapement of the float ball 50 during shipment and installation is precluded. Also, as a result, assembly of the combined liquid level indicator and hydrometer is rendered substantially more convenient and economical from a labor standpoint than prior art structures.

While a particular embodiment of the present invention has been shown and described, modifications may be made, and it is therefore intended to cover in the appended claims all such changes and modifications which fall within the true spirit and scope of the invention.

The invention is claimed as follows:

1. A combined liquid level indicator and hydrometer comprising: a light transmitting member having an outer indicating surface and reflector surface means adapted to be submerged in liquid for reflecting light to said indicating surface when the liquid is below a predetermined level; chamber means comprising an upper means and a lower means, said upper means being connectable to said member and said lower means defining a chamber which is connected to said upper means and having access means of a predetermined size in alignment with said member and positioned for submersion in said liquid, and a float smaller than said predetermined size and of a predetermined specific gravity captured in said lower chamber and moveable between upper and lower positions in accordance with the relative specific gravity of the liquid, said lower chamber being initially formed in an open condition and lockable thereafter for capturing said float within said lower chamber, said lower chamber including hinged closure means carrying at least one moveable wall arranged to pivot between an opened position and a closed locked position to form one of the walls for capturing said float within said lower chamber, and said chamber means including means for locating said float in one of said positions adjacent said access means for viewing said float through said indicating surface and for locating said float in the other of said positions for obscuring the float from view.

2. A combined liquid level indicator and hydrometer as defined in claim 1 wherein said lower chamber means includes a pair of parallel vertically inclined wall means for locating said float in said upper and lower positions and wherein said hinged closure means includes one of said wall means.

3. A combined liquid level indicator and hydrometer as defined in claim 1 wherein said chamber means includes latch means for locking said hinged closure means in said closed position.

4. A combined liquid level indicator and hydrometer as defined in claim 3 wherein said latch means includes a slot within the outer periphery of said lower chamber and an extension protruding laterally from one of the walls carried by said hinged closure means and dimensioned to be lockingly received within said slot.

5. A combined liquid level indicator and hydrometer as defined in claim 1 wherein said upper means includes an aperture dimensioned for lockingly receiving said member and aligning said member with said access means.

6. A liquid condition indicator comprising: a light transmitting member having an outer indicating surface and reflector surface adapted to be submerged in liquid; chamber means comprising an upper means and a lower means, said upper means including connecting means for connecting said member to said upper means and said lower means forming a lower chamber, access means within said lower chamber aligned with said member; a float within said lower chamber and moveable between a first position viewable through said member responsive to a first condition of the liquid and a second position out of view of said member responsive to a second condition of the liquid; and said lower chamber including hinged closure means moveable between an opened position for receiving said float into said lower chamber and a closed position for capturing said float within said lower chamber, said hinged closure means being operative independently of said conecting means of said upper means.

7. A combined liquid level indicator and hydrometer comprising: light transmitting means including indicating means and reflector means adapted to be submerged in liquid for reflecting light to said indicating means when the liquid is below a predetermined level; a float member having a predetermined diameter; chamber means aligned with said reflector means and arranged to confine and position said float member relative to said reflector means for being viewed through said indicating means responsive to the relative specific gravity of the liquid; and connection means for supporting said light transmitting means and aligning said reflector means with said chamber means, said chamber means including hinged closure means operative independently of said connection means and pivotal between an opened position and a closed position for confining said float member within said chamber means.

8. A combined liquid level indicator and hydrometer as defined in claim 7 wherein said connection means is integrally formed with said chamber means.

9. A combined liquid level indicator and hydrometer as defined in claim 8 wherein said connection means includes a collar having a bore dimensioned for tightly receiving said light transmitting means and aligned with an aperture having a diameter greater than said predetermined diameter which communicates with said chamber means, said collar aligning said reflector means with and blocking said aperture communicating with said chamber means.

* * * * *